(12) United States Patent
Darley et al.

(10) Patent No.: US 7,988,507 B2
(45) Date of Patent: Aug. 2, 2011

(54) FEEDTHROUGH FOR ELECTRICAL CONNECTORS

(75) Inventors: Derek Ian Darley, Cromer Heights (AU); Desmond A. McCusker, Balmain (AU); Dusan Milojevicrg, Westleigh (AU); John L. Parker, Roseville (AU)

(73) Assignee: Cochlear Limited, Macquarie University, NSW ( * ) Notice: Subject to any disclaimer, the term of this patent is extended or adjusted under 35 U.S.C. 154(b) by 176 days.

(21) Appl. No.: 12/025,145

(22) Filed: Feb. 4, 2008

(65) Prior Publication Data

US 2008/0208289 A1    Aug. 28, 2008

Related U.S. Application Data

(62) Division of application No. 10/529,063, filed as application No. PCT/AU03/01288 on Sep. 30, 2003, now Pat. No. 7,396,265.

(30) Foreign Application Priority Data

| Sep. 30, 2002 | (AU) | 2002951734 |
| Sep. 30, 2002 | (AU) | 2002951738 |
| Sep. 30, 2002 | (AU) | 2002951739 |
| Sep. 30, 2002 | (AU) | 2002951740 |

(51) Int. Cl.
*H01R 9/22* (2006.01)

(52) U.S. Cl. .......... 439/909; 439/668; 607/37; 607/119

(58) Field of Classification Search ............... 439/668, 439/909; 607/37, 119
See application file for complete search history.

(56) References Cited

U.S. PATENT DOCUMENTS

| 3,271,625 A * | 9/1966 | Caracciolo ............... 361/735 |
| 3,429,788 A * | 2/1969 | Parstorfer ............... 205/125 |
| 3,478,424 A * | 11/1969 | Meoni ..................... 29/619 |
| 3,497,947 A * | 3/1970 | Ardezzone ............... 29/840 |
| 4,865,562 A * | 9/1989 | Burg et al. ............... 439/395 |
| 4,936,792 A | 6/1990 | Onoue et al. |
| 5,274,917 A | 1/1994 | Corbett, III et al. |
| 5,462,408 A * | 10/1995 | Coffy ..................... 416/134 A |
| 5,782,645 A * | 7/1998 | Stobie et al. ............ 439/289 |
| 5,833,714 A | 11/1998 | Loeb et al. |
| 5,907,893 A | 6/1999 | Zadno-Azizi et al. |
| 5,967,841 A | 10/1999 | Bianca et al. |
| 6,179,659 B1 | 1/2001 | Moden |

(Continued)

FOREIGN PATENT DOCUMENTS

DE    41 39 440 A1    6/1993

(Continued)

OTHER PUBLICATIONS

Supplementary European Search Report, EP 03 74 7701, dated Feb. 20, 2007.

(Continued)

*Primary Examiner* — Truc T Nguyen
(74) *Attorney, Agent, or Firm* — Kilpatrick Townsend & Stockton LLP

(57) ABSTRACT

A method (10) of forming an electrically conducting feedthrough. The method (10) comprises a first step (11) of forming an electrically conductive structure (21) comprising a sacrificial component and a non-sacrificial component. At least a portion of the non-sacrificial component can then be coated with a relatively electrically insulating material (35) prior to removal of at least a portion of the sacrificial component from the electrically conductive structure. The structure of the feedthrough provides electrical connection through the wall of a housing of an implantable component while preventing unwanted transfer of materials between the interior of the component and the surrounding environment.

30 Claims, 15 Drawing Sheets

U.S. PATENT DOCUMENTS

| | | |
|---|---|---|
| 6,206,735 B1 | 3/2001 | Zanolli |
| 6,219,247 B1 * | 4/2001 | Haupt et al. .................. 361/707 |
| 6,336,269 B1 | 1/2002 | Eldridge et al. |
| 6,414,835 B1 | 7/2002 | Wolf et al. |
| 6,517,476 B1 * | 2/2003 | Bedoya et al. .................. 600/25 |
| 6,638,121 B1 | 10/2003 | Walker et al. |
| 6,764,336 B2 * | 7/2004 | Ma et al. ....................... 439/604 |
| 6,765,779 B2 * | 7/2004 | Stevenson et al. ............ 361/302 |
| 7,396,265 B2 | 7/2008 | Darley et al. |
| 2001/0039374 A1 | 11/2001 | Schulman |

FOREIGN PATENT DOCUMENTS

| | | |
|---|---|---|
| JP | 63-274074 | 11/1988 |
| JP | 2001-009841 | 1/2001 |
| JP | 2001-052780 | 2/2001 |
| JP | 2002-119435 | 4/2002 |
| JP | 2003-317892 | 11/2003 |

OTHER PUBLICATIONS

Ziaie, B., et al, "A hermetic glass-silicon micropackage with high-density on-chip feedthroughs for sensors and actuators" Journal of Microelectromechanical Systems, Sep. 1996.

Rousche, R F., et al., "Flexible Polyimide-Based Intracortical Electrode Arrays with Bioactive Capability" IEEE Trans. On Biomedical Engineering, vol. 48, No. 3, Mar. 2001.

Petersen, Kurt E., "Silicon as a Mechanical Material," Proceedings of the IEEE, vol. 70, No. 5, May 1982.

International Search Report. PCT/AU03/01288. Mailed Oct. 31, 2003.

Japanese Office Action dated Sep. 30, 2008 for Application No. 2004-538572.

Examiner's First Report for AU2003266816, mailed Apr. 17, 2007, 2 pages.

Examiner's First Report for AU2009200093, mailed May 19, 2010, 2 pages.

Communication Pursuant to Article 94(3) EPC for EP03747701.5 mailed Nov. 6, 2008, 5 pages.

Communication with Supplementary European Search Report for EP03747701.5, mailed Feb. 27, 2007, 3 pages.

International Preliminary Examination Report for PCT/AU2003/001288, for Jan. 18, 2005, 5 pages.

* cited by examiner

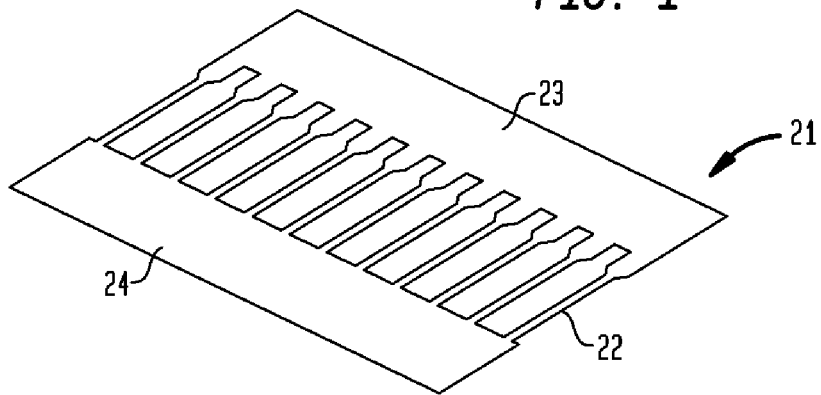
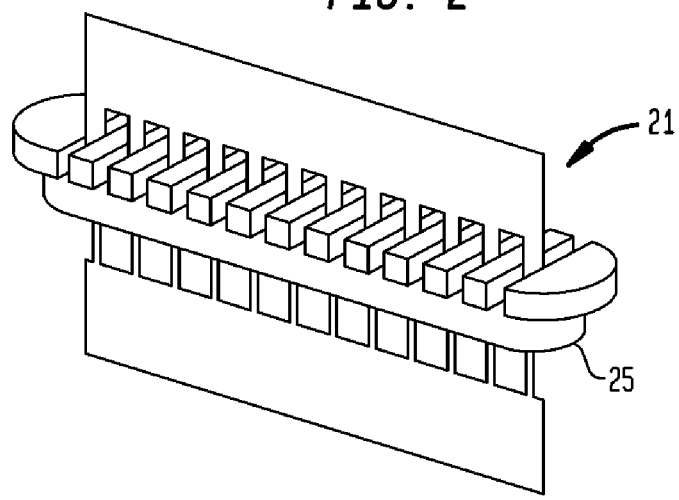
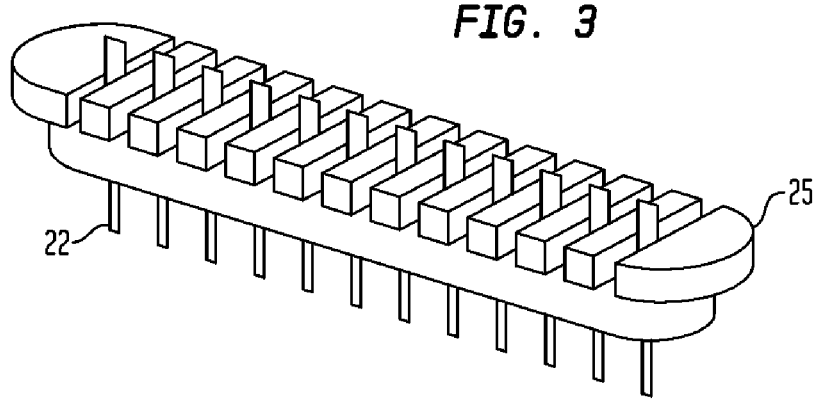

FEEDTHROUGH FOR ELECTRICAL CONNECTORS

CROSS-REFERENCE TO RELATED APPLICATIONS

This application is a divisional of U.S. patent application Ser. No. 10/529,063, entitled "Feedthrough For Electrical Connectors," filed on Nov. 8, 2005 which claims the priority of and is a national stage application of PCT Application No. PCT/AU2003/001288, entitled, "Feedthrough for Electrical Connectors," filed on Sep. 30, 2003, which claims the priority of Australian Patent No. 2002951734, Australian Patent No. 2002951738, Australian Patent No. 2002951739, and Australian Patent No. 2002951740 that were each filed on Sep. 30, 2002. The entire disclosure and contents of the above applications are hereby incorporated by reference.

FIELD OF THE INVENTION

The present invention relates to a method of forming relatively small or miniature electrical connector systems. More specifically, the present invention relates to a method of forming hermetically sealed but electrically conducting feedthroughs for devices, including biosensors and implantable devices. Electrically conducting feedthroughs are also described. Examples of implantable devices that can use such feedthroughs include the implantable component of a cochlear implant hearing prosthesis.

BACKGROUND OF THE INVENTION

The term 'feedthrough' as used herein refers to the provision of an electrically conducting path extending through an insulative member, from one side of the insulative member to another. The electrically conducting path may extend from the interior of a hermetically sealed container or housing on one side of the insulative member, to an external location outside the container or housing on the other side of the insulative member. Typically, a conductive path is provided by an electrically conductive pin, which is electrically insulated from the container or housing by an electrically insulating body surrounding the pin.

A feedthrough device can therefore allow one or more electrical connections to be made with electronic circuitry or components within an hermetically sealed container or housing, whilst protecting the circuitry or components from any damage or malfunction that may result from exposure to the surrounding environment.

There are many applications for feedthrough devices that provide an electrically conducting path through the wall of a housing or container whilst also sealing the electrical container or housing from its ambient environment. Historically, the first such devices were widely used in vacuum technology allowing for the transfer of signals between chambers of differing pressures. In such applications, the vacuum tubes had to be sealed because they could only operate under low-pressure conditions.

Over time, and with the advent of electrical devices capable of being implanted in body tissue to provide therapy to a patient, such as cardiac pacemakers, defibrillators and cochlear implants, the need to provide feedthrough devices with improved hermeticity has become increasingly important. As the environment of living tissue and body fluids is relatively corrosive and devices may contain materials which may be detrimental if exposed to the patient, a hermetic feedthrough device is used to provide a barrier between the electronic components of the device and the external corrosive environment of the human body. With implantable medical devices in particular, it is critically important that the hermetic seal of the device be physically rugged and long lasting. For this reason, stringent requirements are imposed on the hermeticity of an implanted device, typically requiring a seal that provides a leakage rate of less than $10^{-8}$ cc/sec.

Given this, feedthroughs used in medical implant applications, such as those used in pacemaker devices and cochlear implants, typically consist of a ceramic or glass bead that is bonded chemically at its perimeter through brazing or the use of oxides, and/or mechanically bonded through compression, to the walls of the sealed package. A suitable wire or other conductor passes through the centre of the bead, and this wire or conductor must also be sealed to the bead through chemical bonds and/or mechanical compression. Such feedthroughs are typically cylindrical and the wire(s) or conductor(s) mounted within the bead are centred or mounted in a uniform pattern, centrally within the bead.

Other materials and processes are known for making feedthroughs which rely, for example, on use of aluminium oxide ceramic and binders. These types of feedthroughs are widely used for cardiac implants and cochlear implants. One of the processes for making such a feedthrough consists of pre-drilling holes in a sintered ceramic plate and then forcing electrical conductive pins through the holes. While useful, this method is tedious and slow and does not necessarily guarantee a hermetic seal and generally results in unsatisfactory leakage rates on testing and low yields. A second method involves inserting the conductive pins into an unsintered (or 'green') ceramic plate and then curing the assembly by firing to achieve a hermetic seal. A major disadvantage of this last method is that, historically the manufacturing process has been performed by hand. Such a method of manufacture can lead to inaccuracies and be time consuming, expensive and labour intensive. Moreover, the feedthrough devices resulting from such a process do not necessarily have precisely positioned electrical conductors, with the position of the conductors being greatly dependent upon the process itself. Further, as the conductors are typically wires being of a general cylindrical shape and configuration, the size and shape of the conductor extending from the insulative material of the feedthrough is generally the same as the conductor embedded in the insulative material of the feedthrough.

As implantable devices continue to develop and become thinner, smaller and more electronically sophisticated, the requirements of the feedthrough have also increased. In cochlear implants, for example, where there is presently typically somewhere between 22-24 electrode leads, there is a need for 22-24 conductive pins passing through the feedthrough device. As the desire for more electrodes and smaller feedthroughs increases, the demands placed upon the design of the traditional feedthrough also increases. The problems in fabricating such a feedthrough device on such a large scale are therefore quite significant, especially when one considers the relatively high degree of labour intensity and specialisation of current fabricating methods.

While the above described prior art feedthrough devices and fabrication methods have proven successful, it is a relatively slow and labour intensive process to manufacture such devices. The method of manufacture of the feedthrough also presents limitations as to the construction of the feedthrough.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

SUMMARY OF THE INVENTION

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The present invention is directed to a method of forming a feedthrough that preferably addresses at least some of the problems with prior art processes.

The present invention also potentially allows more flexibility in the design of feedthrough devices by providing control over the position and configuration of the conductors through the device, the physical shape and size of the device, the number of conductors used and the overall hermeticity of the feedthrough device.

According to a first aspect, the present invention is a method of forming an electrically conducting feedthrough comprising the steps of:

(i) forming an electrically conductive structure comprising a sacrificial component and non-sacrificial component;

(ii) coating at least a portion of the non-sacrificial component with a relatively electrically insulating material; and (iii) removing at least a portion of the sacrificial component from the electrically conductive structure.

The electrically insulating material is preferably a ceramic material or a hermetic glass material suitable for use in a feedthrough application.

In one embodiment, the electrically insulating material can be coated on the non-sacrificial component and not coated or moulded on to any portion of the sacrificial component of the conductive structure. In another embodiment, the electrically insulating material can be coated on the non-sacrificial component and at least a portion of the sacrificial component of the conductive structure. Still further, step (iii) can comprise removing at least that portion of the sacrificial component on to which the insulative material has not been coated.

In one embodiment, the electrically conductive structure can be formed from an electrically conductive material. The electrically conductive material can be a metal, a metal alloy, an electrically conductive ceramic, an electrically conductive composite, or an intrinsically or extrinsically electrically conductive polymer. In a preferred embodiment, the structure is formed from a film or shim of electrically conductive material. In one such embodiment, the electrically conductive structure can be formed from a film or shim of platinum. Use of other materials such as iridium can be envisaged.

The film or shim can be formed into a shape comprising the sacrificial component and the non-sacrificial component of the electrically conductive structure. In this embodiment, it will be appreciated that that portion of the film or shim comprising the non-sacrificial component may comprise more than one portion of the film or shim. Similarly, that portion of the film or shim comprising the sacrificial component may comprise more than one portion of the film or shim.

In one embodiment, the electrically conductive component may comprise a film or shim having a shape comprising two or more separated conductive elements extending between respective transverse support members. These conductive elements can be substantially elongate. In a further embodiment, the film or shim can have at least ten separated substantially elongate members extending between the respective support members. In one embodiment, the support members are substantially parallel with respect to each other. Still further, the support members can be straight and in a parallel arrangement. In another embodiment, at least one, and preferably all, of the conductive elements can be non-linear. In another embodiment, at least one, and preferably all, of the conductive elements can have a length that is greater than the shortest distance between the respective transverse support members. In a still further embodiment, the surface of at least one, and preferably all, of the conductive elements can be non-linear and/or define an interface path between the conductive element and the insulating material that is longer than the shortest distance between the respective transverse support members.

The separation of the conductive elements is preferably such that the electrically insulating material can be coated between the elements and so prevent electrical conduction between the respective elements at completion of the method according to the first aspect.

In a preferred embodiment, the shape of the electrically conductive component can be formed in step (i) by punching the shape, using a suitably shaped and dimensioned punching tool, from a film of electrically conductive material, such as platinum.

In another embodiment, the shape of the electrically conductive component can be formed in step (i) by using electrical discharge machining (EDM), which is also known as spark erosion, to remove unwanted portions of the film. In a preferred embodiment, the EDM equipment used in the process has a cutting tool comprising an electrode. The cutting tool does not physically cut the sheet but instead relies on the equipment generating a series of electrical discharges between the electrode and the film in a dielectric fluid. The electrical discharges serve to vaporise the film in the region adjacent the cutting tool.

In a preferred embodiment, the cutting tool has a size and shape that matches the size and shape of the portion of the film to be removed from the film during the machining steps. In this embodiment, it is preferred that the tool is brought adjacent the film at a number of different locations so as to remove differing portions of the film. This multiple use of the tool preferably serves to gradually build up the pattern of the electrically conductive component.

In a preferred embodiment, the cutting tool can be used to form a series of discrete linear conductive members from a film of platinum or other suitable metal or metal alloy. The linear conductive members can be aligned in a parallel arrangement.

In another embodiment, the cutting tool can be used to form a series of discrete linear conductive members from a plurality of films of platinum or other suitable material stacked one atop the other. In this manner, a large number of electrically conductive components can be prepared with a single cutting motion of the cutting tool. In such an embodiment, a method known as "wire cutting" can be employed. This method operates in a similar manner to EDM/spark erosion methods wherein a wire is passed through a stack of films or foils of conductive material with this wire becoming the electrode causing the erosion of material adjacent the electrode. By using this method a plurality of films or foils can be patterned simultaneously, resulting in a process that is capable of mass producing patterned conductive films or foils to be used to create the feedthrough device of the present invention.

In the method, at least a portion of each of the substantially elongate members extending between the support members are coated with the electrically insulating material (step (ii) is described in more detail below). As mentioned, the electrically insulating material can be alumina but other suitable ceramic types can be envisaged.

In another embodiment, the step of forming the electrically conductive structure can comprise the steps of:

(a) forming a relatively electrically insulating disc having an outer periphery defining a plurality of outwardly extending teeth having notches therebetween; and (b) winding an electrically conductive element around the disc such that at least some of the notches have a portion of the conductive element passing therethrough.

In this embodiment, the electrically insulating disc can be formed of a ceramic material such as alumina. The disc can have a plurality of equally spaced notches and teeth about its outer periphery.

In this embodiment, each of the notches can receive a conductive element. Preferably, a single metal wire is used for each disc. The wire preferably comprises platinum wire. The wire can have a diameter of about 25 µm.

Once the conductive element has been wound about the disc and passed through each of the notches, the insulating disc and surrounding conductive element can be overmoulded with a coating of insulating material as defined in step (ii) of the method described above. Those portions of the conductive element not extending through the feedthrough can then be removed.

In a still further embodiment, the step of forming the electrically conductive structure comprises a step of forming a sheet of platinum having a plurality of integrally attached substantially elongate members extending outwardly from at least a portion of the periphery thereof. In a preferred embodiment, the elongate members extend outwardly and in a direction out of the plane of the sheet. For example, the elongate members can extend outwardly and upwardly from the sheet. In this embodiment, the elongate members can be rectangular in shape.

In this embodiment, the sheet can be rectangular or square. In this embodiment, at least three sides of the sheet can have elongate members extending at least out of the plane of the sheet.

In a still further embodiment, the step of forming the electrically conductive structure comprises a step of spirally coiling an electrically conductive wire, such as platinum wire, along at least a portion of a length of a screw thread. Once positioned, an insulating layer can be moulded around the thread and the wire. Once the insulating layer has cured, the screw thread can be withdrawn from the insulating material so leaving the coiled wire embedded within the inner surface of the insulating layer.

The step of coating the electrically conductive structure preferably comprises a step of mounting or clamping the conductive structure in a mould and then moulding a coating of the insulating material on and/or around the conductive structure.

Where the conductive structure comprises a plurality of substantially elongate members formed from a film or shim of, for example, platinum, the insulating material is preferably coated or moulded around at least a portion of the substantially elongate members of the conductive structure. In this embodiment, said portion of the substantially elongate members comprises a portion of the non-sacrificial component of the electrically conductive structure. While this embodiment envisages the film or shim being shaped as desired prior to clamping or mounting in the mould, it will be appreciated that a film could be firstly mounted or clamped in the mould and then shaped or punched as required prior to the moulding or coating step.

Where the conductive structure comprises an insulative disc having a notched outer surface and a conductive element passing through the notches around the disc, the insulating material is preferably moulded around the disc such that at least those portions of the conductive element passing through the notches of the disc outer surface are encapsulated in the insulating material.

Where the conductive structure comprises a sheet having a plurality of substantially elongate members extending at least out of the plane of the sheet, the insulating material is preferably moulded to both sides of the sheet and elongate members, thereby encapsulating at least a portion of the members in the insulating material.

Where the conductive structure comprises a coiled wire embedded within the inner surface of an insulating layer, the orifice left by the withdrawal of the screw thread can be filled with insulating material.

In a preferred embodiment, the mould can comprise an injection mould. In one embodiment, step (ii) of the method can comprise a step of using powder injection moulding (PIM) to mould the insulating material around the desired portion of the conductive structure.

In this moulding process, insulating material such as fine ceramic powder is mixed with a carrier chemical, typically called binder, and homogenised to create a feedstock for the injection mould. The presence of the binder serves to make the feedstock sufficiently fluid to be used in an injection moulding process. Once moulded, the insulating material can be allowed to at least partially set. The resulting moulded part is hereinafter called the green body.

Once the green body is formed, the sacrificial component of the electrically conductive structure can be removed. During this step, it is possible that a portion of the green body may also need to be removed. In one embodiment, the sacrificial component can be removed by being cut, abraded or ground away. In this regard, physical cutting with a knife, or laser cutting techniques, are envisaged.

Where the electrically conductive structure comprises the plurality of substantially elongate members extending between the transverse members, the sacrificial component preferably includes at least the transverse support members so leaving a plurality of electrically insulated elongate members extending through the green body.

Where the electrically conductive structure comprises an insulating disc having a conductive element, such as a wire, passing through a plurality of notches, the sacrificial component can comprise at least some of that part of the conductive element not passing through the notches. On removal of the remainder of the conductive element, one is left with an insulative member having a conductive member passing therethrough at each location where a notch existed in the outer surface of the original insulative disc.

Where the electrically conductive structure comprises a sheet having a plurality of substantially elongate members extending at least out of the plane of the sheet, the sacrificial component preferably comprises the sheet from which each of the elongate members extend. With the sheet and substantially elongate members supported on one side by an insulative layer, the sheet can be punched from the structure leaving a ring of insulating material with the now separated elongate conductive members supported thereon. Another layer of insulating material can then be moulded between and around the ring thereby forming an insulating member having the elongate members extending therethrough from one face to the other.

Where the electrically conductive structure comprises a coiled wire embedded within an insulating coating, the sacrificial component preferably comprises adjacent portions of respective turns of the coiled wire.

In a still further embodiment, the method can comprise an additional step of debinding the green body. In this step, any binder in the green body is preferably extracted from the insulative material. In one embodiment, this step can comprise a chemical debinding in which the green body is soaked in a suitable solvent. In another embodiment, this step can comprise exposing the green body to a relatively elevated temperature. This temperature is preferably sufficient to boil off the binder from the green body while not causing the green body to undergo sintering. In one embodiment, the temperature is between about 150° C. and 200° C.

During the debinding step, the insulating material preferably shrinks in dimension. This debinded insulating material member is hereinafter called a brown body.

When ready, the brown body can undergo a sintering step. The sintering step preferably comprises exposing the brown body to a suitable elevated temperature. In one embodiment, the sintering step can comprise exposing the brown body to a sintering temperature of about 1700° C. During the sintering step, the insulating member undergoes further shrinkage and becomes relatively more robust. The shrinkage of the insulating member also serves to form a hermetic seal at the interface between the embedded conductive members and the surrounding sintered insulating member.

Once complete, the insulating member with the conductive members extending therethrough can be brazed into an orifice in the wall of a unit adapted to receive the feedthrough. Electrical connection can then be made to each end of the respective conductive members as required to form respective electrical conductive paths through the insulating body of the feedthrough.

According to a further aspect, the present invention is a feedthrough formed using one of the methods described herein.

According to a still further aspect, the present invention is a feedthrough comprised of one or more relatively electrically conductive structures extending through and embedded within a relatively electrically insulating body, wherein the one or more electrically conductive structures are formed from a film or shim of an electrically conductive metal or metal alloy.

In one embodiment, the electrically conductive structures have an overall elongate length of at least 7 mm and, more preferably, about 7.8 mm. In a further embodiment, the width of the conductive structures is preferably between about 1.5-2.5 mm. In a still further embodiment, the film or shim from which the conductive structures are formed preferably has a thickness of between about 40 and 70 microns, more preferably about 50 microns.

In one embodiment of this aspect, the electrically conductive structures can be formed using one of the methods according to the first aspect of the invention.

According to yet another aspect, the present invention is an electrically conducting feedthrough comprising:

a relatively electrically insulating member having a first face and at least a second face; and at least one electrically conductive member extending through at least a portion of the electrically insulative member from the first face to the second face;

wherein said at least one conductive member is non-linear between said first face and said second face.

According to yet a further aspect, the present invention is an electrically conducting feedthrough comprising:

a relatively electrically insulative member having a first face and at least a second face; and at least one relatively electrically conductive member extending through at least a portion of the electrically insulative member from the first face to the second face;

wherein said at least one conductive member has a length between said first face and second face that is greater than the shortest distance between said first face and said second face.

According to a still further aspect, the present invention is an electrically conducting feedthrough comprising:

a relatively electrically insulative member having a first face and at least a second face; and at least one relatively electrically conductive member having an outer surface and extending through at least a portion of the electrically insulative member from the first face to the second face;

wherein at least a portion of the outer surface of said at least one conductive member is non-linear between said first face and said second face.

According to yet another aspect, the present invention is an electrically conducting feedthrough comprising:

a relatively electrically insulative member having a first face and at least a second face; and at least one relatively electrically conductive member having an outer surface and extending through at least a portion of the electrically insulative member from the first face to the second face;

wherein at least a portion of the outer surface of said at least one conductive member defines an interface path between the conductive element and the insulating material that is greater than the shortest distance between said first face and said second face.

In one embodiment, the first face and second face of the insulating member can face outwardly in opposite directions. In one embodiment, the first and second faces can be substantially parallel or parallel. The first face is preferably the outer face of the feedthrough and the second face is preferably the inner face of the feedthrough.

In one embodiment, the feedthrough preferably has a plurality of electrically conductive members extending through the insulative member from said first face to said second face. In one embodiment, each of the conductive members has the same configuration. In another embodiment, only some of the conductive members may have the same configuration while one or others have a different configuration.

In a further embodiment, said one or more conductive members can undergo a first change of direction between the first face and the second face of the insulative member. In another embodiment, said one or more conductive members can undergo two or more changes of direction between the first face and the second face of the insulative member.

In yet another embodiment, said one or more conductive members undergo a change of direction in a nominal plane extending at an angle, such as a right angle, to one or both faces of the insulative member. In another embodiment, said one or more conductive members can undergo a change of direction into a direction out of a nominal plane extending at an angle, such as a right angle, to one or both faces of the insulative member. The conductive member can undergo more than one change of direction out of said nominal plane.

Each change of direction can be at a right angle to the preceding direction of the conductive member. In another embodiment, the change of direction can be at a different angle than a right angle to that of the preceding direction.

In another embodiment, the change of direction can be abrupt. In another embodiment, the change of direction can be smoothly curved. In another embodiment, a particular conductive member can undergo a combination of abrupt and/or smoothly curved changes of direction.

In yet another embodiment, said one or more conductive members can have a shape of varying cross-section over the length thereof. In this regard, the conductive members may extend linearly or non-linearly through the insulative member, however, the interface path between the conductive members and the insulative member is maximised, thereby reducing the effective leakage pathway of the feedthrough device. The conductive members may have a stepped shape providing a zig-zag interface pathway or may have a screw-thread shape providing an equally extended interface pathway.

According to another aspect, the present invention is an electrically conducting feedthrough comprising:

a relatively electrically insulating member having a first face and at least a second face; and a plurality of electrically conductive members each having a first end and a second end and extending through at least a portion of the insulative member from said first end at or adjacent the first face to said second end at or adjacent the second face of the insulative member;

wherein the configuration of the first ends of the conductive members at or adjacent the first face of the insulative member is different to the configuration of the second ends of the conductive members at or adjacent the second face of the insulative member.

In this aspect, the respective configurations of the first ends and the second ends of the conductive members can be such that the number of first ends of the conductive members per a defined unit area at or adjacent the first face of the insulative member is different to the number of second ends of the conductive members per said defined unit area at or adjacent the second face of the insulative member.

In one embodiment, the number of first ends per defined unit area can be greater than the number of second ends per said defined unit area. In another embodiment, the number of first ends per defined unit area can be less than the number of second ends per said defined unit area.

In this embodiment, the defined unit area can be 1 mm$^2$, 1 cm$^2$, or some other area.

Still further, the respective configurations of the first ends and the second ends of the conductive members can be such that the spacing between the first ends of the conductive members at or adjacent the first face of the insulative member is different to the spacing between the second ends of the conductive members at or adjacent the second face of the insulative member.

In this embodiment, the spacing between the first ends of the conductive members can be greater than the spacing between the second ends of the conductive members. In another embodiment, the spacing between the first ends of the conductive members can be less than the spacing between the second ends of the conductive members.

In each of these aspects, the feedthrough can comprise two or more groups of said plurality of electrically conductive members. Each conductive member in a group can be identical in configuration to the other conductive members in a group. In another embodiment, at least one conductive member in a group can be different in configuration to one or all of the other conductive members in that group. In another embodiment, the conductive members of one group can be different in configuration to one or more of the conductive members of another group of the feedthrough. Still further, the conductive members of one group can be identical in configuration to one or more of the conductive members of another group of the feedthrough.

In one embodiment, each feedthrough comprises two, three or more groups of conductive members. Each group can comprise a series of conductive members in side-by-side relationship. This embodiment offers the capability of the feedthrough having a plurality of layers of conductive members. Such layers of conductive members can be off-set from adjacent layers.

In yet another embodiment, the respective dimensions and shape of the first ends and second ends of the conductive members can be such that their shape and dimensions can differ between the first ends at or adjacent the first face of the insulative member and the second ends at or adjacent the second face of the insulative member. Equally, the shape and dimensions of the first and second ends of the conductive members can also differ from the shape and dimensions of the conductive member embedded within the insulative member.

In this embodiment, the shape and dimensions of the first ends of the conductive members can be such as to allow the ends to communicate directly with an integrated chip design whilst the shape and dimensions of the second ends of the conductive members can be such as to allow the ends to communicate with wires or leads connected to a stimulating electrode or the like. In this regard, the size and shape of the first and second ends of the conductive members can be determined prior to the manufacture of the feedthrough device.

In these aspects, the relatively electrically insulative material is preferably a ceramic material or hermetic glass material, suitable for use in a feedthrough application.

Still further, the hermeticity of the interface between each of the interfaces between the respective electrically conductive structures and the relative insulative body or the degree of permeation of fluid between the conductive structure and the insulative body is preferably defined by the following relationship:

$$H=f(L,1/A,1/t) \qquad (1)$$

where

L is the length of the electrically conductive element extending from a first face to a second face of the insulative body;

A is the cross-sectional area of the electrically conductive element; and t is the time that the interface is exposed to the fluid, including bodily fluids.

It will be appreciated that the cross-sectional area A is related to a measurement of the perimeter of the electrically conductive element. That is, the smaller the size of the interface between the conductive insert and the insulative material, the greater the degree of hermeticity of the feedthrough.

In one embodiment, the feedthrough can be brazed into the wall of an electrical device, such as an implantable stimulator unit of a medical implant device. In a preferred embodiment, the feedthrough can be adapted to be used with a cochlear implant hearing prosthesis to provide electrical conduction between the circuitry within an implantable stimulator unit and the intracochlear or extracochlear electrodes and/or the implantable receiver coil.

Each feedthrough preferably has sufficient conductive members embedded therein to ensure there are sufficient connectors to suit the desired application. In a cochlear implant application, the feedthrough would preferably have sufficient conductive members embedded therein to ensure that there are sufficient connectors for each of the electrode channels of the intracochlear electrode array, one or more extracochlear electrodes, and the inputs from the receiver coil.

The present invention provides a method of forming a feedthrough for an implantable component comprising a relatively electrically insulative member having a plurality of relatively electrically conductive members extending therethrough. The method ensures the electrically conductive members are hermetically encased within the insulating material in a way that allows electrical connection through the feedthrough while preventing transfer of bodily fluids from outside the component into the interior of the component, as well as preventing the transfer of potentially dangerous materials from internal of the component to the surrounding tissue and body fluids.

The present invention also provides the capability of using smaller sized conductive components, having a smaller perimeter of the cross section, thereby providing increased hermeticity. It is therefore possible to utilise the present invention to create feedthrough devices that are of similar dimensions to prior art feedthrough devices but which have far superior hermeticity properties. Equally, the present invention can be utilised to create feedthrough devices which are of much smaller dimensions than existing feedthrough devices having similar and improved hermeticity than is currently the case.

The present invention also provides the ability to create a feedthrough device having a relatively denser array of conductive structures than prior art devices, as the conductive components can be spaced closer together than is achievable in traditional devices.

According to a further aspect, the present invention is a method of forming an insulative member of a feedthrough device comprising the step of moulding the member in a mould having a plurality of pins extending therethrough.

In this embodiment, the mould can have a desired number of pins, for example 28, in one plate of the mould and a corresponding number of cavities, accommodating the pins, in the opposite plate of the mould. In use, the mould is filled with hot feedstock and in order to prevent the pressure of the injection from bending the pins and to minimize impact during injection, the mould is only partially opened when the initial quantity of the feedstock is injected. As the mould cavity is only partially opened, only a very short portion of the pins are exposed to the pressure. The mould is then slowly opened while injection continues, so that at any given time only a very short portion of the pins are exposed unsupported to the injection of the feedstock. Eventually, the entire cavity of the mould is filled while the position of the pins is preserved. Once the moulding step is concluded, the moulded part can be ejected from the mould, leaving behind the mould with its elongate pins in place.

The moulded part ejected from the mould is left with a plurality of holes therein formed by the presence of the pins in the mould. The holes can be about 175 µm in diameter.

The moulded part can then undergo further processing. For example, platinum pins can be inserted into the holes of the moulded part before the entire assembly undergoes a water de-binding step, which includes washing of the moulded part over several hours at an elevated temperature, eg. 40° C. The assembly can then undergo thermal de-binding at approximately 300° C. over a period of approximately 24 hours. Finally, the assembly can be sintered at around 1600° C. thereby forming a final assembly that has a series of platinum pins extending therethrough.

In another aspect, the present invention is a method of forming an insulative member of a feedthrough device comprising the steps of:

forming a sacrificial component having a plurality of elongate structures;

coating at least a portion of the elongate structures with a relatively electrically insulating material; and sacrificing the sacrificial component so leaving an electrically insulating material having a plurality of holes therein at what was the location of the elongate structures.

In this aspect, the sacrificial component can have a shape similar to or identical to that depicted in FIGS. 1, 14, 15, 16, 17 and 20. Other shapes, such as annular arrangements of elongate structures can be envisaged. In this embodiment, however, the entire component is adapted to be sacrificed so leaving a formed insulative member having a plurality of holes extending therethrough corresponding to the position of the elongate members of the sacrificed component.

In one embodiment, the sacrificial component can comprise a metal or polymer having a melting point less than that of the insulative member formed therearound. Once the insulative member is formed, the temperature of the member can be increased until such time as the metal or polymer of the sacrificial component melts and is drained or drawn away from the insulative member. In this regard, it will be appreciated that the insulative member could be formed using an annular sacrificial component that is melted away so leaving the member with its holes formed in the location of the now melted sacrificial component.

BRIEF DESCRIPTION OF THE DRAWINGS

By way of example only, preferred embodiments of the invention are now described with reference to the accompanying drawings, in which:

FIG. 1 is a perspective view of one embodiment of an electrically conductive structure for use in the method according to the present invention;

FIG. 2 is a perspective view of the conductive structure of FIG. 1 overmoulded with an insulative ceramic member;

FIG. 3 is a perspective view of the feedthrough formed from the conductive structure of FIG. 1;

FIG. 6 is a feedthrough formed from the conductive structure of FIG. 4a;

FIG. 12b is a top view of a platinum sheet highlighting the region of platinum to be removed in the process depicted in FIG. 12a;

FIG. 12c is a top view of machined sheet of platinum formed using the process depicted in FIG. 12a;

PREFERRED MODE OF CARRYING OUT THE INVENTION

Figure 11:
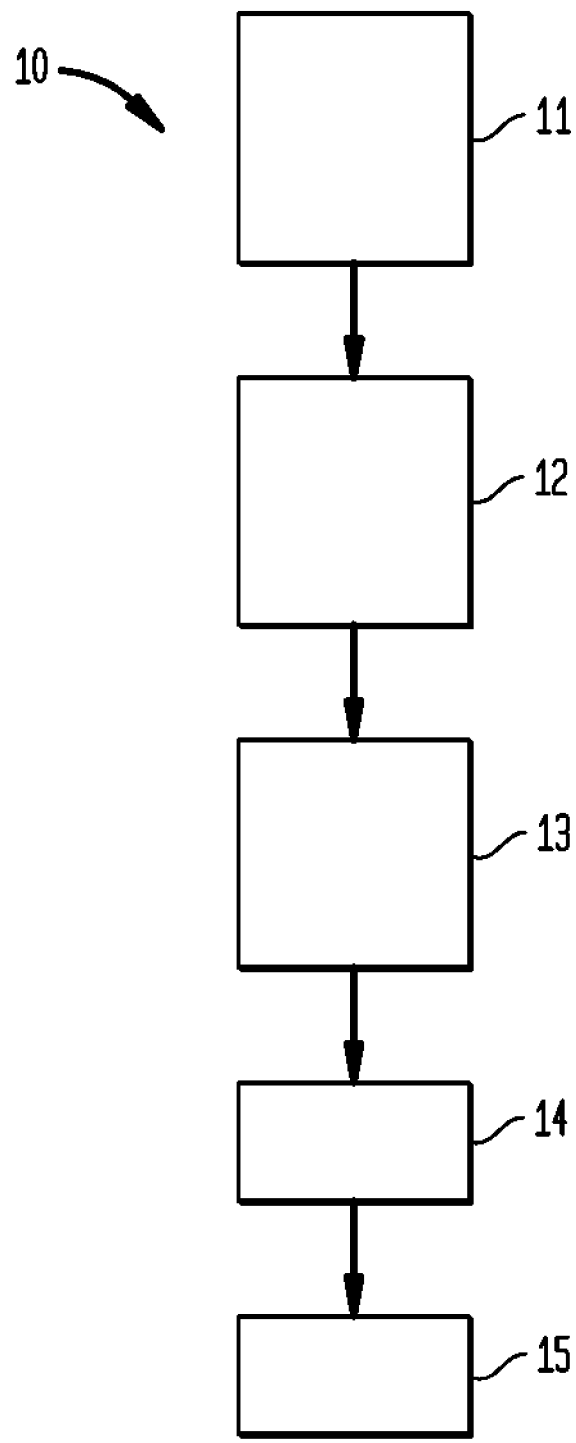
FIG. 11 is a simplified flow chart of the steps of one embodiment of the method according to the present invention.

The steps of one embodiment of a method of forming an electrically conducting feedthrough according to the present invention are depicted in FIG. 11.

The method 10 comprises a first step 11 of forming an electrically conductive structure comprising a sacrificial component and non-sacrificial component. Different examples of such structures are depicted in FIGS. 1, 4b, 7, and 10b.

The method further comprises a step 12 of coating or moulding a non-electrically conductive insulative member on to at least a portion of the non-sacrificial component and not on to at least a portion of the sacrificial component of the conductive structure.

Still further, the method comprises a step 13 of then removing at least that portion of the sacrificial component of the conductive structure on to which the insulative member has not been coated or moulded.

Following removal of the sacrificial component of the conductive structure, the green body of the insulator can undergo a step of debinding 14 prior to a step of sintering 15. Once sintered, the ceramic feedthrough with the conductive members extending therethrough is ready for appropriate mounting in the wall 278 of an implantable stimulator unit 276 of a cochlear implant hearing prosthesis 270 or other appropriate device.

The above sequence of steps are generally governed by the properties of the insulative member being employed, for example, ceramic shrinks when sintered. In this regard, it may be possible to vary the sequence of the steps so that removal of at least a portion of the sacrificial component occurs after de-binding or sintering of the ceramic.

As depicted in FIG. 1, the electrically conductive structure formed in step 11 can be formed from a film or shim 21 of biocompatible platinum. Other suitable electrically conductive metals or metal alloys are also envisaged.

As depicted in FIG. 1, the film or shim 21 of platinum can be formed into a shape comprising the sacrificial component and the non-sacrificial component of the electrically conductive structure. In this embodiment, the electrically conductive structure comprises a plurality of separated elongate linear members 22 extending between respective parallel transverse support members 23,24.

The separation of the elongate members 22 is such that the insulative material when moulded around the members 22 can also move between the members 22 and so prevent electrical conduction between the respective members 22 at completion of the method 10.

In the depicted embodiment, the shape of the electrically conductive structure 21 is formed by punching the shape, using a suitable shaped and dimensioned punching tool, from a film of platinum. It is envisaged that this shape could be created by a variety of material removal methods, such as electrical discharge machining (EDM), micro-knifing and/or laser cutting.

Figure 12A:
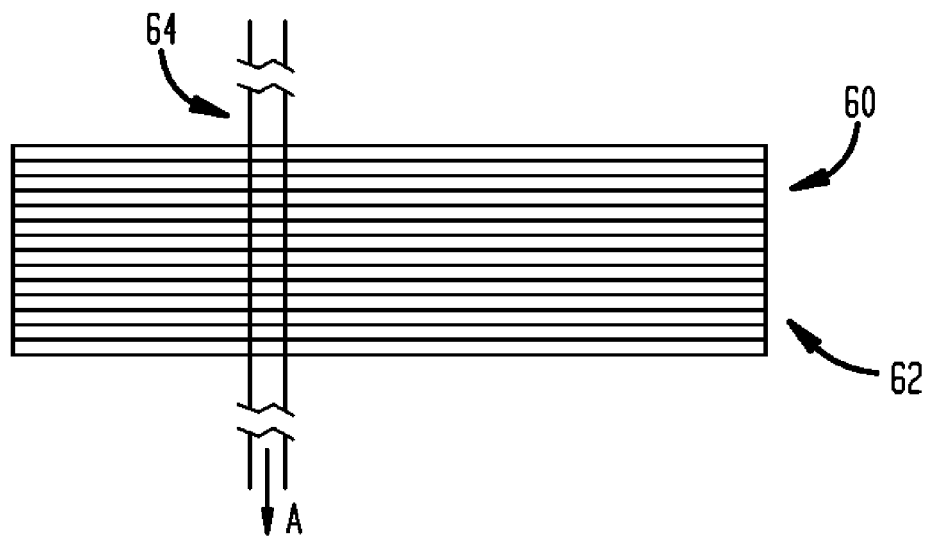
FIG. 12a is a side view of a stack of platinum sheets about to be machined into an electrically conducting feedthrough according to the present invention.
Figure 12B:
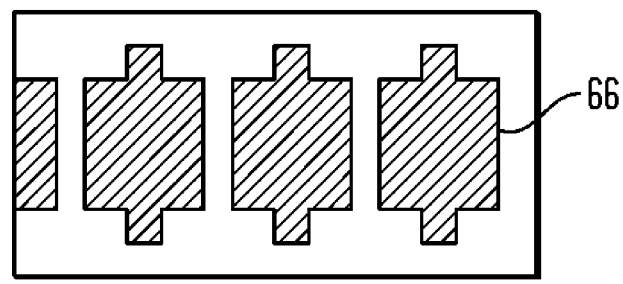
Figure 12C:
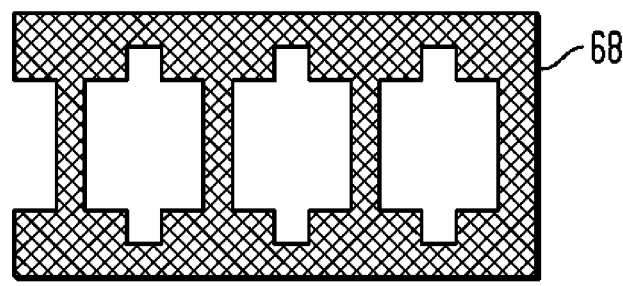

FIGS. 12a, 12b and 12c depict one method of forming the electrically conductive structure according to a preferred embodiment. In this method, wire cutting is utilised. This method employs the principles of EDM methods to remove the unwanted material, however, in this instance the spark is created between the work-piece 60 being machined, for example a stack of platinum films 62, and a continuously moving wire 64, with the components immersed in a dielectric medium (not shown).

FIG. 12a is a side view of this method and shows a number of foils of conductive material 62 stacked together to form a work-piece 60, with the foils preferably being clamped together and immersed into a dielectric medium. The foils can be platinum or iridium or any other suitable conductive material. The wire 64 is then fitted through the work-piece 60 by creating an appropriate aperture through the work-piece 60. A series of electrical discharges are then generated between the wire 64 and the work-piece 60 in the dielectric medium, causing erosion of the films 62 to occur in a desired pattern. Typically, the wire 64 is drawn through the work-piece 60 in a continuous feeding motion, for example in a downward motion shown by arrow A, however, the position of the wire 64 with respect to the work-piece 60 can remain stationary, while the work-piece 60 is moved in the desired directions to created the desired pattern.

As is shown in FIG. 12b, the hashed regions 66 are removed from each of the foils of conductive material in the work-piece 60. This then leaves a conductive film as depicted in FIG. 12c as the cross-hashed region 68, which is substantially the same as that shown and described with reference to FIG. 1.

It is also envisaged that the electrically conductive structures as depicted in the drawings can be formed by metal injection moulding (MIM). Like PIM described above for forming the electrically insulative layer, MIM uses metal powder instead of ceramic powder as in PIM, to create feedstock. In MIM, the structure is moulded and then undergoes de-binding and sintering to form the final structure. Such a method of forming the structure may be particularly useful in forming structures with complex three-dimensional shapes, such as those described below. MIM may also be particularly useful in forming structures having various cross-sectional shapes. In this regard, MIM techniques can form structures having different profiles and smoother finishes than can currently be achieved with the above mentioned material removal methods.

As depicted in FIG. 2, at least a portion of each of the elongate members 22 extending between the support members 23,24 are coated or overmoulded with an insulative material 25 described in more detail below.

In the depicted embodiment, the step of moulding the insulative material 25 around the electrically conductive structure (step 12) comprises a step of mounting or clamping the conductive structure in a mould and then moulding the insulative material on and/or around the conductive structure.

In a preferred embodiment, the mould can comprise an injection mould. In one embodiment, step 12 can comprise a step of using powder injection moulding (PIM) to mould the insulative material around the desired portion of the conductive structure. In a preferred embodiment of this moulding process, fine ceramic powder is mixed with a binder and homogenised to create a feedstock for the injection mould. The presence of the binder serves to make the feedstock sufficiently fluid to be used in an injection moulding process. Once moulded, the insulative ceramic can be allowed to at least partially set and form a green body.

Once the green body is formed, the sacrificial component of the electrically conductive structure can be removed. In the embodiment depicted in FIGS. 1 to 3, the sacrificial component can be removed by laser cutting. Other suitable material removal techniques, such as cutting or abrading techniques are also envisaged.

In the embodiment depicted in FIGS. 1 to 3, the sacrificial component comprises the transverse members 23,24. Once these are removed, a plurality of respectively electrically insulated elongate members 22 remain extending through the green body 25.

Figure 4A:
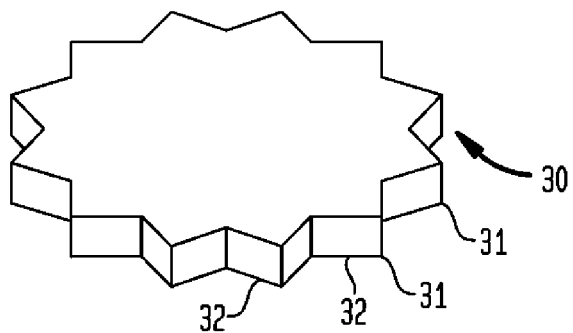
FIG. 4a is a perspective view of an insulative ceramic disc having a saw-tooth outer surface for use in the formation of another embodiment of a conductive structure according to the present invention.
Figure 4B:
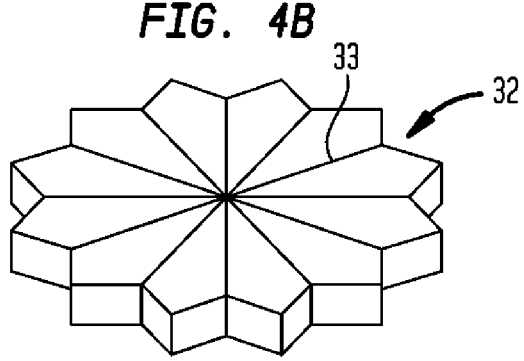
FIG. 4b is a perspective view of the ceramic disc of FIG. 4a with a conductive platinum wire coiled around the disc.

In the embodiment depicted in FIGS. 4a and 4b, the step 11 of forming the electrically conductive structure comprises the steps of:

(a) forming an insulative disc 30 having an outer surface defining a plurality of teeth 31 having notches 32 therebetween; and (b) winding a platinum metal wire 33 around the disc 30 such that at least some of the notches 32 have a wire passing therethrough (as is depicted in FIG. 4b).

In the depicted embodiment, the insulative disc can be formed of a ceramic material such as that used in step 12 described above. In another embodiment, a different material could be used that exhibits the desired insulative properties. The insulative disc 30 preferably has a plurality of equally spaced notches and teeth about its outer periphery.

As depicted in FIG. 4b, each of the notches 32 receive a portion of the wire 33. In the depicted embodiment, the wire has a diameter of about 25 μm.

Once the wire 33 has been passed through each of the notches 32, the insulative disc 30 and surrounding wire can be overmoulded in step 12 with an outer annular coating of a suitable insulative material such as a ceramic 35. This material is preferably moulded around the disc such that at least those portions of the wire 33 passing around the notches 32 of the disc outer surface are encapsulated in the material 35.

Figure 5:
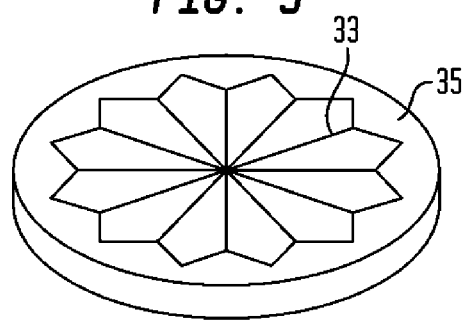
FIG. 5 is a perspective view of the disc of FIG. 4b with an overmould of ceramic material around the outer surface of the disc.
Figure 6:
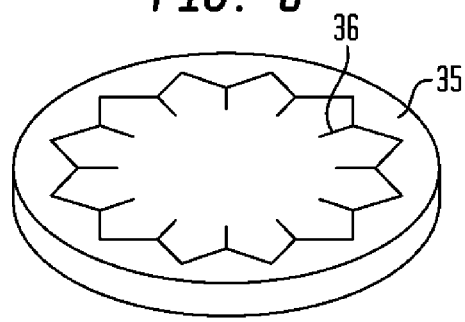

The sacrificial component of the structure depicted in FIG. 5 comprises that part of the wire not passing through the notches 32. On removal of the remainder of the wire, one is left with an insulative member 35 having a platinum conductive member 36 passing therethrough at each location where a notch 32 existed in the outer surface of the original insulative disc 30.

Figure 7:
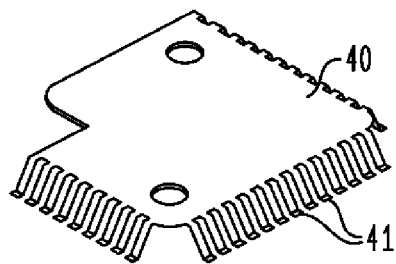
FIG. 7 is a perspective view of a platinum sheet with elongate members extending out of the plane thereof for use as a conductive structure in another embodiment of a method according to the present invention.
Figure 8A:
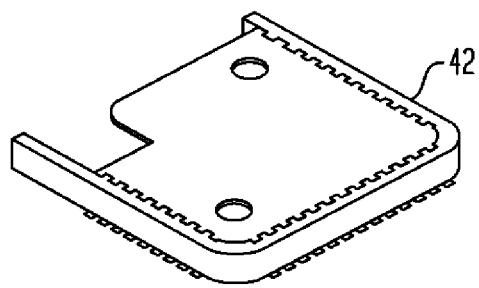
FIGS. 8a and 8b are perspective views of the sheet of FIG. 7 with a layer of ceramic moulded thereto.
Figure 8B:
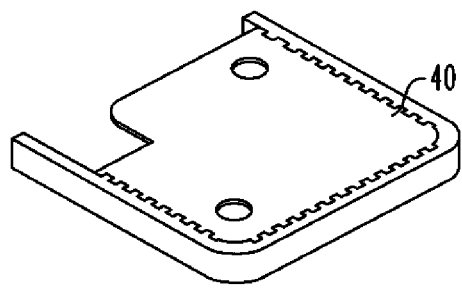
Figure 9:
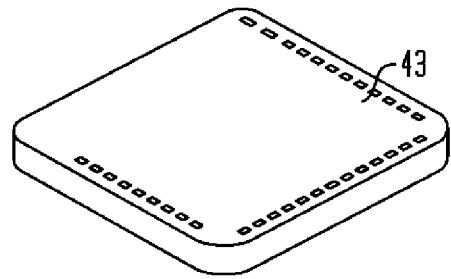
FIG. 9 is a perspective view of a feedthrough formed using the sheet of FIG. 7.

Another method of forming a different conductive structure is depicted in FIGS. 7 to 9. In this arrangement, step 11 comprises forming a multi-sided sheet 40 of electrically conductive material, such as platinum, having a plurality of integrally attached elongate members 41 extending outwardly from at least three sides of the periphery thereof. The elongate members extend outwardly and in a direction out of the plane of the sheet. In the depicted arrangement, the elongate members 41 extend outwardly and upwardly from the sheet.

In this embodiment, a coating of insulative material 42 is firstly moulded to one side of the sheet 40 and elongate members 41.

In this embodiment, the sacrificial component preferably comprises the sheet 40 from which each of the elongate members 41 extend. With the sheet and elongate members supported on one side by a layer of insulative material 42, the sheet 40 can be removed from the structure leaving a ring of insulative material with the now separated elongate members 41 supported thereon. Another layer of insulative material 43 can then be moulded between and around the ring thereby forming an insulative member having the elongate members extending therethrough from one face to the other. The result is a plurality of respectively electrically insulated elongate members 41 embedded within a ceramic green body comprised of layers 42 and 43.

Figure 10A:
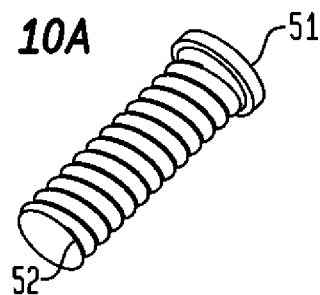
FIGS. 10a-10e are perspective views of a still further embodiment for forming a feedthrough using the method according to the present invention.
Figure 10B:
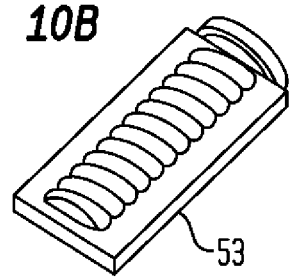
Figure 10C:
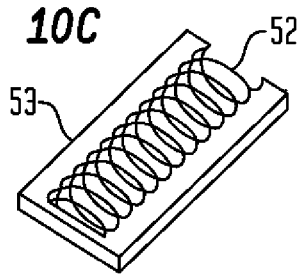
Figure 10D:
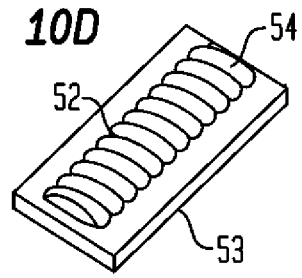
Figure 10E:
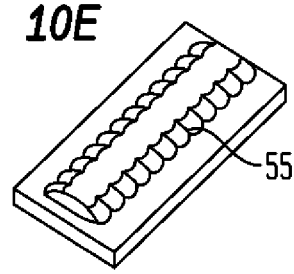

In another embodiment depicted in FIGS. 10a-10e, the step of forming the electrically conductive structure can comprise a step of spirally coiling an electrically conductive wire 52, such as platinum wire, along at least a portion of a length of a thread of a screw 51. Once positioned, a layer of insulative material 53 can be moulded around the thread 51 and the wire 52. Once the insulative material 53 has cured, the screw 51 can be withdrawn from the insulative ceramic material so leaving the coiled wire 52 embedded within the inner surface of the insulator layer 53 (see FIG. 10c). The orifice left by the withdrawal of the screw 51 can be filled with insulative material 54. In this embodiment, the sacrificial component preferably comprises adjacent portions of respective turns of the coiled wire 52, so leaving wire portions 55 embedded within an insulative member as depicted in FIG. 10e.

Figure 13A:
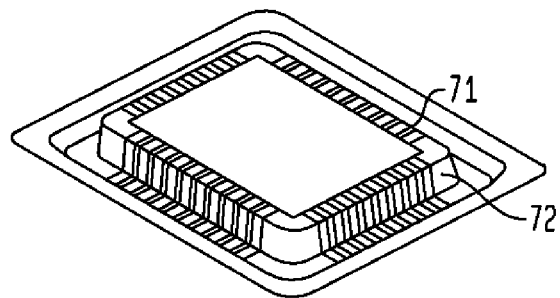
FIGS. 13a-13d depict another possible technique for forming a feedthrough according to the present invention.
Figure 13B:
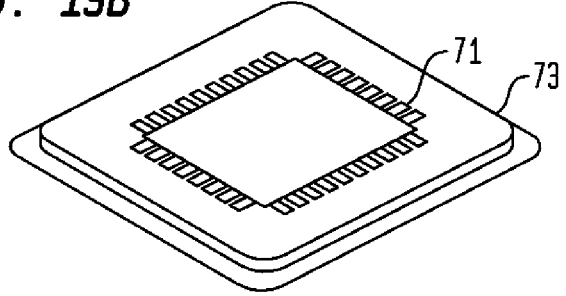
Figure 13C:
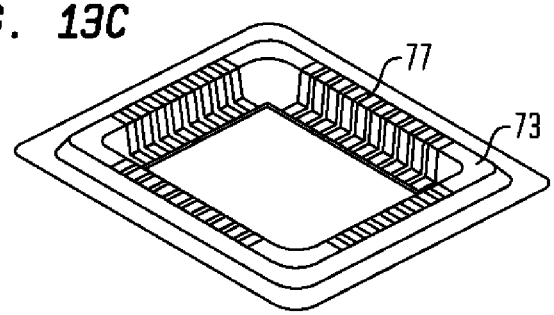
Figure 13D:
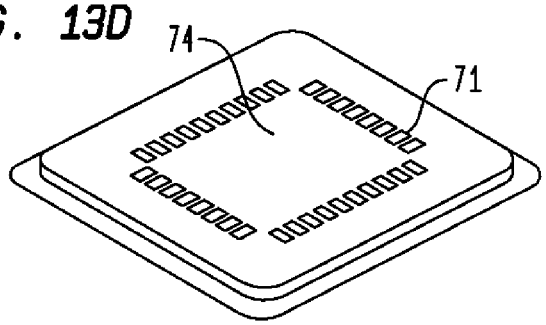

FIGS. 13a-13b depict a still further embodiment of a method for forming a feedthrough according to the present invention. In this embodiment, a series of platinum conductive members 71 are formed on a copper backing 72 (FIG. 13a). A first layer of ceramic 73 can then be moulded thereto (FIG. 13b) before the copper backing is etched away (FIG. 13c). An overmould of ceramic 74 is then provided (see FIG. 13d) to form the completed feedthrough.

Figure 14:
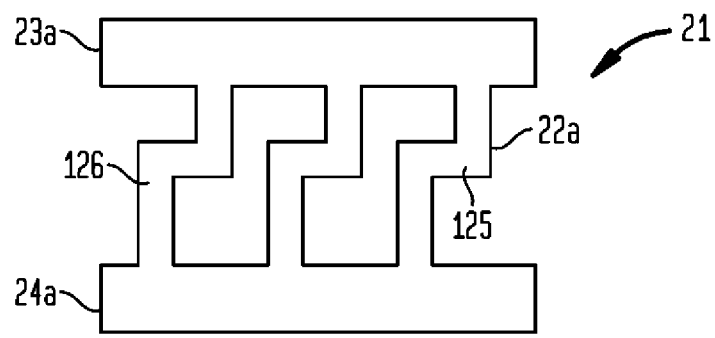
FIG. 14 is a plan view of another embodiment of an electrically conductive structure for use in the method according to the present invention.

FIG. 14 depicts another type of electrically conductive structure that can be used in the manufacture of a feedthrough according to the present invention. The depicted electrically conductive structure is again formed from a film or shim 21 of biocompatible platinum.

In FIG. 14, the film or shim 21 of platinum is formed into a shape comprising a sacrificial component and a non-sacrificial component. In this embodiment, the electrically conductive structure comprises a plurality of separated non-linear members 22a extending between respective parallel transverse support members 23a, 24a.

The separation of the non-linear members 22a is such that the insulative member (such as a ceramic) when moulded around the members 22a can also move between the members 22a and so prevent electrical conduction between the respective non-linear members 22a at completion of the method 10.

In the depicted embodiment, the shape of the electrically conductive structure 21 is formed by punching the shape, using a suitable shaped and dimensioned punching tool, from a film of platinum. It is envisaged that this shape could also be formed by a variety of material removal methods, such as electrical discharge machining (EDM), micro-knifing and/or laser cutting.

FIG. 14 depicts the non-linear members 22a as having two relatively abrupt right angle changes of direction at corners 125 and 126. Alternative elongate but non-linear conductive members 22a are depicted in FIGS. 15, 16, and 17.

Figure 15:
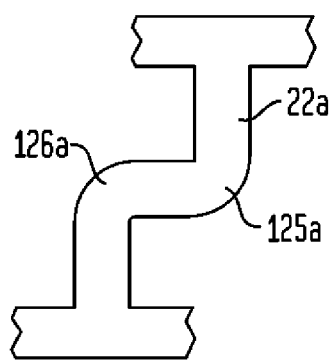
FIG. 15 is an enlarged plan view of a single conductive member of another embodiment of a conductive structure according to the present invention.
Figure 16:
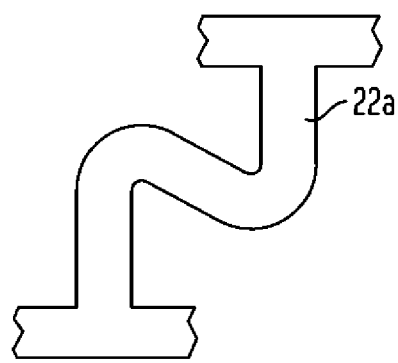
FIG. 16 is an enlarged plan view of a single conductive member of another embodiment of a conductive structure according to the present invention.

In FIG. 15, the non-linear member 22a undergoes two changes in directions at corners 125a and 126a. In this embodiment, the changes in direction are relatively smoothly curved. As depicted in FIG. 16, the non-linear member can undergo more than two changes in direction. Other suitable configurations can be envisaged.

Figure 17:
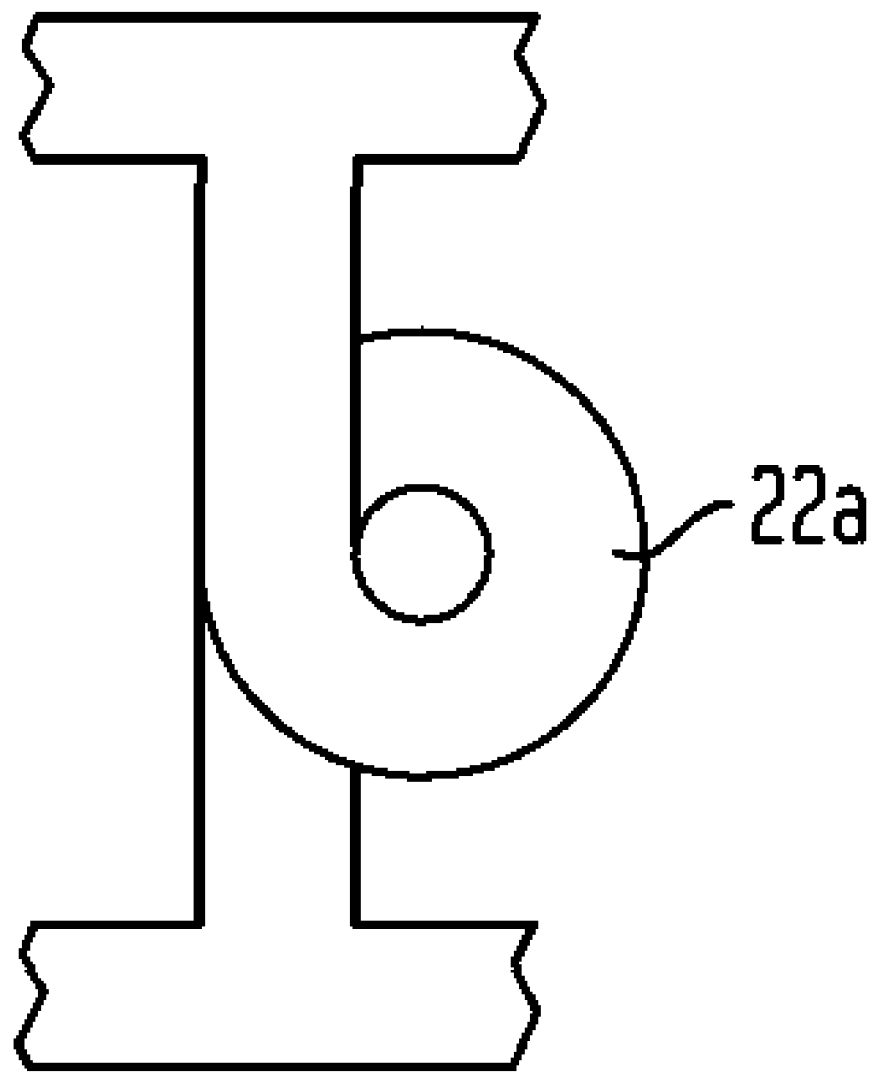
FIG. 17 is an enlarged view of a single conductive member of another embodiment of a conductive structure according to the present invention.

In FIG. 17, the conductive member is formed and then twisted into a third dimension before being clamped and then placed in a mould. The insulative member can then be moulded around the spiral conductive member 22a. Again, other configurations of the conductive member extending through the insulative member in a third dimension can be envisaged.

Figure 18:
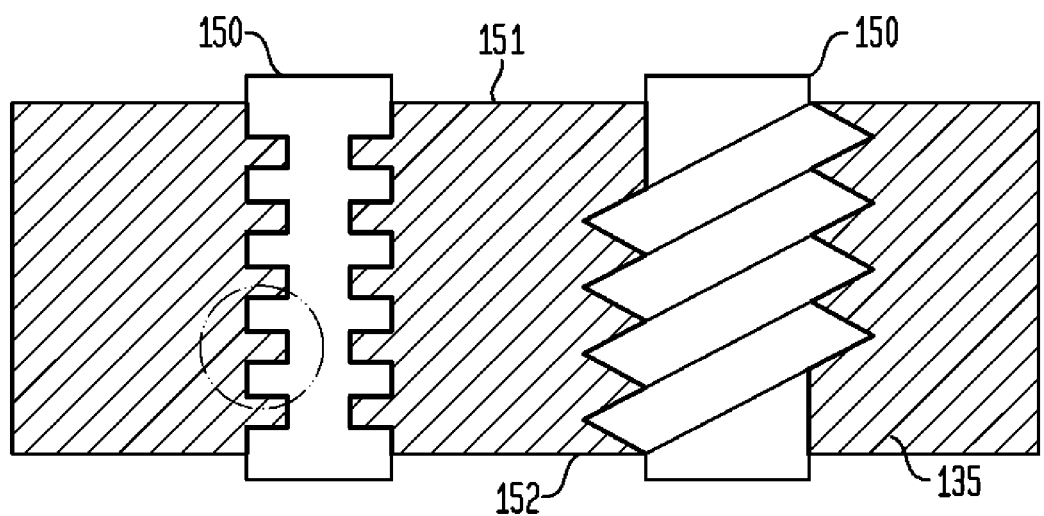
FIG. 18 is a cross-sectional view of two different conductive structures of a feedthrough according to the present invention wherein the interface between the conductive structures and the insulative material is non-linear.

FIG. 18 depicts an alternative embodiment of the present invention. In this embodiment, conductive members 150 are shown extending from one face 151 of an insulative member 135 to another face 152. In this embodiment, the conductive members 150 are substantially linear however the surfaces of the conductive members 150 are provided with extended material to produce a shape that lengthens the interface path between the conductive material and the insulative material 150. As shown, possible shapes of the conductive members according to this embodiment include having a stepped outer surface or a screw-thread shaped member. The purpose of providing such a shaped conductive member is to substantially increase the leakage pathways of the feedthrough device.

In the depicted embodiment, the step of moulding the ceramic 135 around the electrically conductive structure comprises a step of mounting or clamping the conductive structure in a mould and then moulding the ceramic 135 on and/or around the conductive structure.

The mould can again comprise an injection mould. In one embodiment, powder injection moulding (PIM) can be used to mould the ceramic around the desired portion of the conductive structure. In this moulding process, fine ceramic powder is mixed with a binder and homogenised to create a feedstock for the injection mould. The presence of the binder serves to make the feedstock sufficiently fluid to be used in an injection moulding process. Once moulded, the ceramic can be allowed to at least partially set and form a green body.

Figure 19:
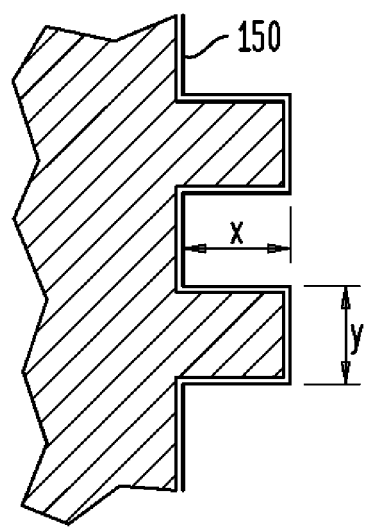
FIG. 19 is an enlarged view of one of the interfaces of FIG. 18.

In the embodiment shown in FIG. 19, the effect of such a design on the feedstock properties is shown. In this embodiment, which is an enlargement of the section shown in FIG. 18, the feedstock is designed to flow inside the stepped cavities of the conductive member to form a bond with the surface of the conductive member along the entire length of the conductive member. In this embodiment, the conductive member can have dimensions of x and y within the range of 10-50 μm. In this range, the feedstock is capable of filling such cavities with standard powder injection moulding techniques to provide a well sealed interface. It is envisaged that with improvements in the capabilities of the feedstock and associated equipment, even smaller cavities will be able to be successfully employed.

Once the green body is formed, the sacrificial component of the electrically conductive structure can be removed. In the depicted embodiment, the sacrificial component can be removed by laser cutting. Other suitable techniques, such as cutting or abrading techniques, are also envisaged.

In the embodiment depicted in FIGS. 14-17, the sacrificial component comprises the transverse members 23a, 24a. Once these are removed, a plurality of respectively electrically insulated non-linear members 22a remain extending through the green body.

Figure 20:
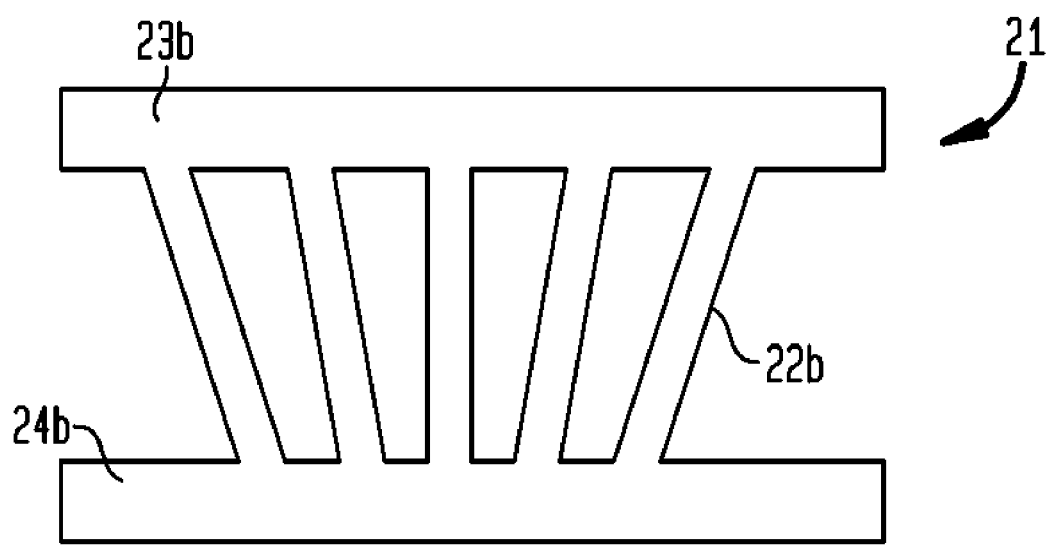
FIG. 20 is a plan view of yet another embodiment of an electrically conductive structure for use in the manufacture of a feedthrough according to the present invention.

FIG. 20 depicts a still further type of electrically conductive structure that can be used in the manufacture of a feedthrough according to the present invention. The depicted electrically conductive structure is formed from a film or shim 21 of biocompatible platinum. Other suitable electrically conductive metals or metal alloys can be envisaged.

In FIG. 20, the film or shim 21 of platinum is formed into a shape comprising a sacrificial component and a non-sacrificial component. In this embodiment, the electrically conductive structure comprises a plurality of separated members 22b extending between respective parallel transverse support members 23b, 24b.

The spacing between the conductive members at their connection to transverse member 23b is larger than the spacing between the conductive members where they connect to transverse member 24b.

While FIG. 20 depicts the members 22b as being straight, it will be appreciated that non-linear members could extend between the respective transverse members 23b, 24b.

The separation of the members 22b is such that the insulative member material when moulded around the members 22b can also move between the members 22b and so prevent electrical conduction between the respective members 22b.

In the embodiment depicted in FIG. 20, the shape of the electrically conductive structure 21 is formed by punching the shape, using a suitable shaped and dimensioned punching tool, from a film of platinum. It is envisaged that this shape could be created by a variety of material removal methods, such as electrical discharge machining (EDM), micro-knifing and/or laser cutting.

In the embodiment depicted in FIG. 20, the step of moulding the insulative ceramic member 235 (see FIG. 21) around the electrically conductive structure comprises a step of mounting or clamping the conductive structure in a mould and then moulding the ceramic on and/or around the conductive structure. The mould can again comprise an injection mould. In one embodiment, powder injection moulding (PIM) can be used to mould the ceramic around the desired portion of the conductive structure. In this moulding process, fine ceramic powder is mixed with a binder and homogenised to create a feedstock for the injection mould. The presence of the binder serves to make the feedstock sufficiently fluid to be used in an injection moulding process. Once moulded, the ceramic can be allowed to at least partially set and form a green body.

Once the green body is formed, the sacrificial component of the electrically conductive structure can be removed. In the depicted embodiment, the sacrificial component can be removed by laser cutting. Other suitable cutting or abrading techniques can be envisaged.

In the embodiment depicted in the drawings, the sacrificial component comprises the transverse members 23b, 24b. Once these are removed, a plurality of respectively electrically insulated members 22b remain extending through the green body 235 as depicted in FIG. 21.

Figure 21:
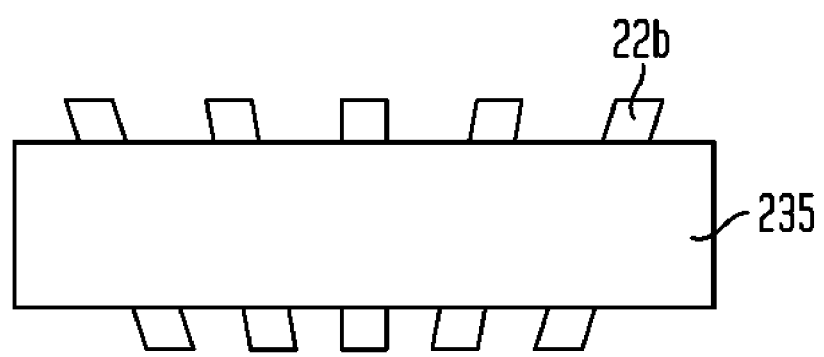
FIG. 21 is a plan view of the electrically conductive structure of FIG. 20 embedded within a ceramic member with its transverse support members removed.

Such a feedthrough as depicted in FIG. 21 can be adapted to be brazed into the wall 278 of an implantable stimulator unit of a cochlear implant hearing prosthesis 270. In this regard, the feedthrough can be adapted to provide electrical conduction between the circuitry within the implantable stimulator unit 276 and the intracochlear or extracochlear electrodes 272, and/or the implantable receiver coil 280.

An advantage of the present invention is that it provides the possibility of allowing exchange of an implantable stimulator unit 276 within a recipient with a newer or replacement model without the necessity to explant the intracochlear electrode array 274. For example, if a recipient already has an implanted stimulator unit 276 with a cochlear array 274 connected thereto and electrical connection provided by a feedthrough, it is possible to disconnect the electrode array 274 from the external side of the feedthrough and then remove the stimulator unit 276. While a newer model stimulator unit 276 may have a different internal and/or external construction, a feedthrough as here depicted can be provided in the housing of the stimulator unit that is connectable on its external side with the existing configuration of the implanted cochlear array 274 but has a different configuration on its internal side that is compatible with the configuration of the internal wiring of the stimulator unit 276.

The conductive members of this feedthrough have a sufficient length and are encased within the insulative member in a way that allows electrical connection through the feedthrough while preventing transfer of bodily fluids from outside the component into the interior of the component and vice versa.

Figure 22:
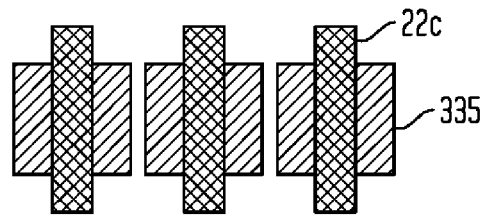
FIG. 22 is a sectional view of another embodiment of a feedthrough having three groups of conductive members.

FIG. 22 depicts a feedthrough that comprises three separate groups of conductive structures 22c disposed in a parallel arrangement. While each group of conductive structures depicted in FIG. 22 is made of a conductive structure, such as is depicted in FIG. 20, it will be appreciated that the feedthrough could be formed of three conductive structures depicted in FIG. 1 or three conductive structures depicted in FIG. 14. Alternatively, the feedthrough could be formed of one each of the conductive structures depicted in FIGS. 1, 14 and 20, respectively. Still further, the feedthrough might be formed of two of one structure of either FIG. 1, 14 or 20 and one of the others depicted in these figures.

Figure 23:
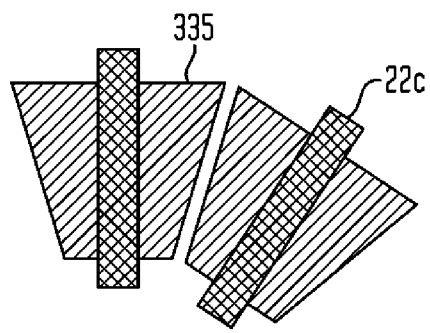
FIG. 23 is a sectional view of another embodiment of a feedthrough according to the present invention.

As depicted in FIG. 23, the respective groups of conductive structures 22c need not be mounted in a parallel configuration. Again, the respective groups of conductive members 22d can be formed from various combinations of conductive structures as depicted in FIG. 1, 14 or 20 or other structures within the scope of the invention.

Figure 24:
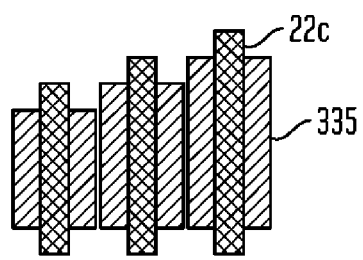
FIG. 24 is a sectional view of a still further embodiment of a feedthrough according to the present invention.
Figure 25:
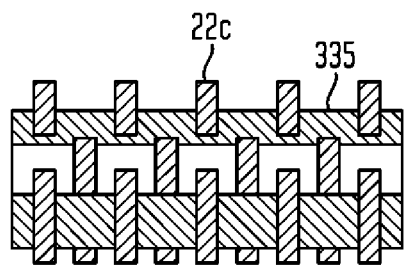
FIG. 25 is a further part-sectional, part front view of the feedthrough of FIG. 24.

FIGS. 24 and 25 depict a further embodiment where the length of the conductive members of each group is different to the length of the members in an adjacent group. The conductive members of a group are also offset from its adjacent groups. While the groups are in a parallel relationship, it will be appreciated that the groups could be in a non-parallel relationship as depicted in FIG. 23. Each of the conductive members is also depicted as linear and parallel to other members within its group. Again, it can be envisaged that instead, the conductive members may have different configurations, such as is depicted in FIG. 14 or 20. Such configurations make it possible to provide connections in 3 dimensions, increasing the density of the connecting elements.

In this embodiment, the platinum members 22c are embedded in a surrounding sintered insulative member 335.

Once complete, the insulative member 335 with the platinum members 22c extending therethrough can be brazed into an orifice in the wall of a unit adapted to receive the feedthrough. Electrical connection can then be made to each end of the respective platinum members as required to form respective electrical conductive paths through the insulative body of the feedthrough.

Such a feedthrough can be adapted to be brazed into the wall 278 of an implantable stimulator unit 276 of a cochlear implant hearing prosthesis 270. In this embodiment, the feedthrough can be adapted to provide electrical conduction between the circuitry within the implantable stimulator unit 276 and the intracochlear or extracochlear electrodes 272, and/or the implantable receiver coil 280.

Each feedthrough preferably has sufficient platinum members embedded therein to ensure there are sufficient connectors for each of the electrode channels of the intracochlear electrode array 274, one or more extracochlear electrodes, and the inputs from the receiver coil.

Figure 26:
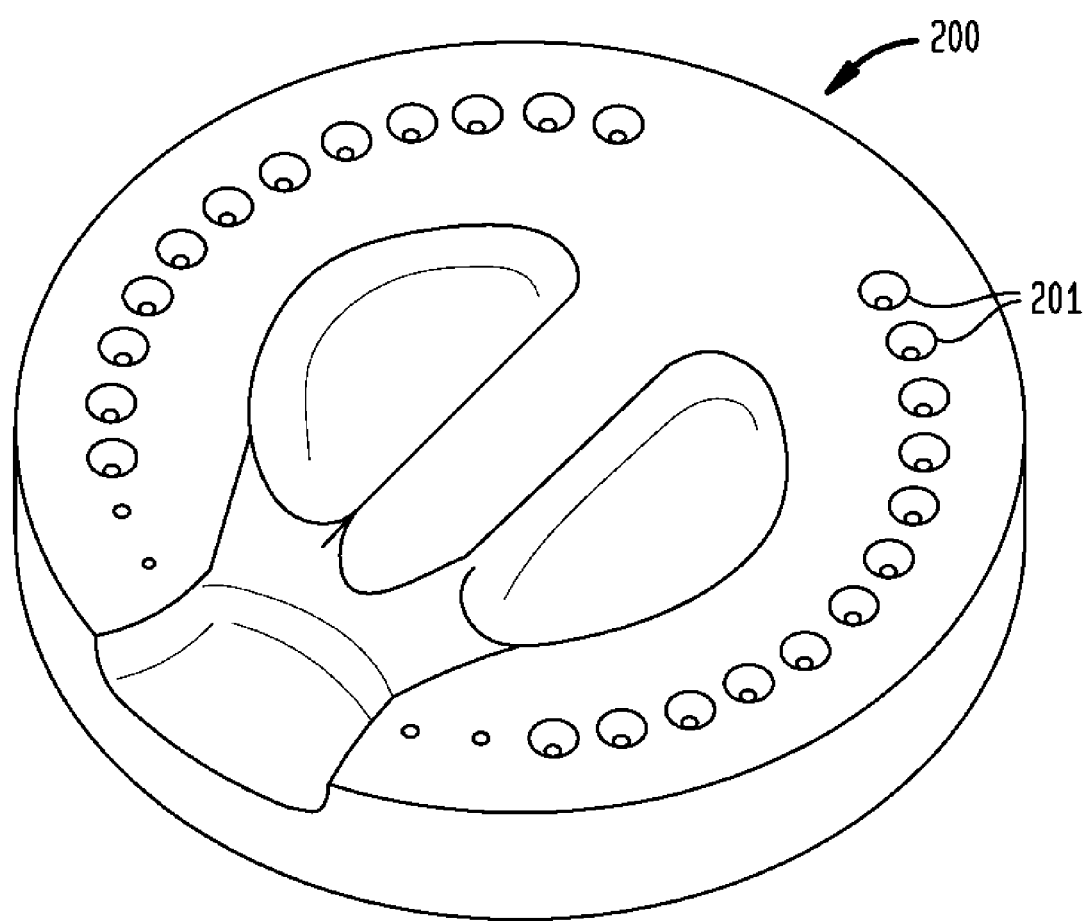
FIG. 26 is a perspective of another embodiment of an insulative member according to the present invention.
Figure 27:
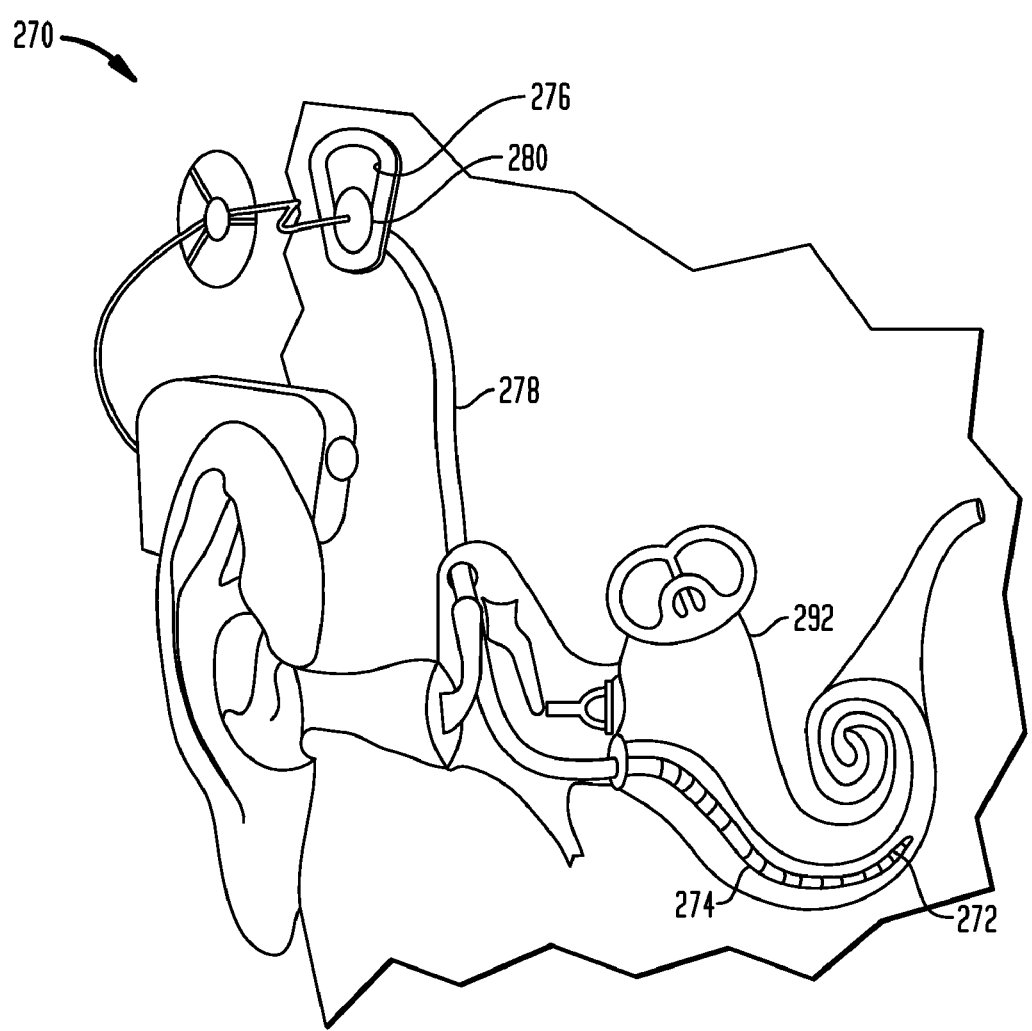
FIG. 27 is a perspective view of an implantable medical device to which a feedthrough according to the present invention is electrically coupled.
Figure 28A:
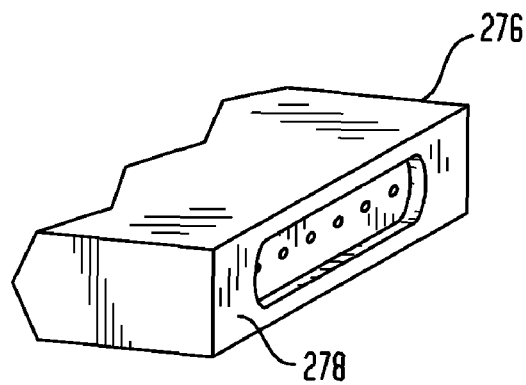
FIG. 28a is a partial perspective view of an implantable medical device to which a feedthrough according to the present invention is electrically coupled.
Figure 28B:
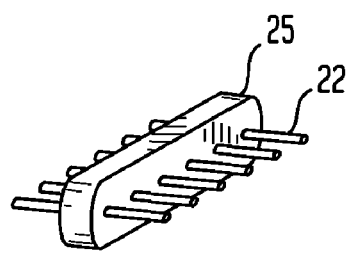
FIG. 28b is a perspective view of an embodiment of a feedthrough according to the present invention.
Figure 28C:
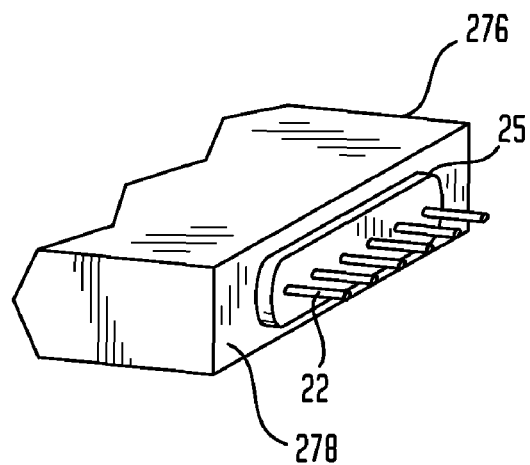
FIG. 28c is a partial perspective view of an implantable medical device after a feedthrough according to the present invention has been electrically coupled.

FIG. 26 depicts yet another embodiment of the present invention, wherein the feedthrough is formed in a similar manner to that described above, particularly in relation to FIGS. 1-3, however in this embodiment the entire conductive structure is sacrificial, leaving a insulative member 200 having a plurality of holes 201 extending therethrough.

In this specific embodiment, the insulative body 200 is formed using powder injection moulding and features 28 holes, in predetermined positions, extending therethrough.

The insulative body 200 is preferably moulded as described previously. However, in this embodiment, the mould features 28 pins in one plate of the mould and a corresponding number of cavities, accommodating the pins, in the opposite plate of the mould. In use, the mould is filled with hot feedstock and in order to prevent the pressure of the injection from bending the pins and to minimize impact during injection, the mould is only partially opened when the initial quantity of the feedstock is injected. As the mould cavity is only partially opened, only a very short portion of the pins are exposed to the pressure. The mould is then slowly opened while injection continues, so that at any given time only a very short portion of the pins are exposed unsupported to the injection of the feedstock. Eventually, the entire cavity of the mould is filled while the position of the pins is preserved. Once the moulding step is concluded, the moulded part 200 is ejected, leaving behind the mould with its elongate pins in place. The moulded part 200 ejected from the mould features the 28 holes 201. Preferably, the holes 201 are only 175 μm in diameter. The moulded part 200 then undergoes further processing.

Platinum pins, are firstly inserted into the holes 201 of the moulded part 200 and the entire assembly undergoes a water de-binding step, which includes washing of the moulded part over several hours at 40° C. The assembly then undergoes thermal de-binding at approximately 300° C. over a period of approximately 24 hours. Finally, the assembly is sintered at around 1600° C. thereby forming a final assembly that has a series of platinum pins extending therethrough.

Another embodiment of an insulative member having a plurality of holes extending therethrough can be formed using a modified method from that set out in FIG. 11. In this embodiment, the method comprises a step of moulding or coating an electrically insulating material around a structure, such as a structure having a shape similar to or identical to that depicted in FIGS. 1, 14, 15, 16, 17 and 20. In this embodiment, however, the entire structure is adapted to be sacrificed so leaving a formed insulative member having a plurality of holes extending therethrough corresponding to the position of the sacrificed structure.

In one embodiment, the sacrificial structure can comprise a metal or polymer having a melting point less than that of the insulative member formed therearound. Once the insulative member is formed, the temperature of the member can be increased until such time as the metal or polymer of the sacrificial structure melts and is drained or drawn away from the insulative member. In this regard, it will be appreciated that the insulative member 200 could be formed using an annular sacrificial structure that is melted away so leaving the member 200 with its holes 201 formed in the location of the now melted sacrificial structure.

The present invention provides a method of forming a feedthrough for an implantable component comprising an insulative member having a plurality of electrically conductive members extending therethrough. The method ensures the electrically conductive members are encased within the insulative member in a way that allows electrical connection through the feedthrough while preventing unwanted transfer of materials between the interior of the component and the surrounding environment.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A feedthrough for an implantable medical device comprising:
an electrically insulating body including a first surface and a second surface; and
one or more electrically conductive structures configured to contiguously extend through and be embedded within said electrically insulating body, such that each of said one or more electrically conductive structures are circumferentially covered by said electrically insulating body, such that opposing ends of said at least one electrically conductive structures are exposed, and such that said at least one electrically conductive structures extend beyond at least the first or second surface,
wherein the one or more electrically conductive structures comprise an electrically conductive metal or metal alloy and have a thickness of a film of the same electrically conductive metal or metal alloy.

2. The feedthrough of claim 1 wherein the electrically insulating body is formed of a ceramic.

3. The electrically conducting feedthrough of claim 1, wherein respective configurations of first ends and second opposite ends of the one or more electrically conductive structures are such that the spacing between the first ends of the electrically conductive structures at or adjacent the first surface of the insulating body is different from the spacing between the second ends of the electrically conductive structures at or adjacent the second face of the insulating body.

4. The electrically conducting feedthrough of claim 3, wherein the dimension and/or shape of the first ends of said conductive structures are different from the dimension and/or shape of the second ends of the conductive structures.

5. The feedthrough of claim 1, wherein the electrically insulating body has a first face into which one of said one or more electrically conductive structures enter the electrically insulating body and a second face out of which the one of said one or more electrically conductive structures exit the electrically insulating body, wherein at least a portion of the outer surface of said conductive structures defines an interface path between the one of said one or more electrically conductive structures and the insulating material that is equal in length to the shortest distance between said first face and said second face when the faces are parallel to each other.

6. The feedthrough of claim 1, wherein the electrically insulating body has a location of entry into which one of said one or more electrically conductive structures enter the electrically insulating body and a location of exit out of which the one of said one or more electrically conductive structures exits the electrically insulating body, wherein the one of said one or more electrically conductive structures have a length between said location of entry and said location of exit that is equal to the shortest distance between the location of entry and the location of exit.

7. The feedthrough of claim 1, comprising a plurality of electrically conductive structures, wherein said electrically conductive structures are circumferentially covered by said electrically insulating body such that a hermetic seal is formed between the electrically conductive structures and the electrically insulating body.

8. The implantable medical apparatus of claim 1, wherein the one or more electrically conductive structures are formed from a film or shim of the electrically conductive metal or metal alloy.

9. The implantable medical apparatus of claim 1, wherein the one or more electrically conductive structures comprise shims of the electrically conductive metal or metal alloy.

10. The feedthrough of claim 1, wherein:
the one or more electrically conductive structures are in direct contact with the electrically insulating body; and
the electrically insulating body is a monolithic body.

11. The feedthrough of claim 7, wherein the hermetic seal is located at least an interface between the embedded electrically conductive members and the surrounding insulating member.

12. The feedthrough of claim 7, wherein the hermetic seal is adapted to prevent transfer of fluids from a first side of the feedthrough into which the one or more electrically conductive structures enter the electrically insulating body to a second side of the feedthrough out of which the one or more electrically conductive structure exit the electrically insulating body.

13. The feedthrough of claim 7, wherein the hermetic seal is adapted to prevent transfer of fluids from a first side of the feedthrough into which the one or more electrically conductive structures enter the electrically insulating body, along one or more of the electrically conductive structures, to a second side of the feedthrough out of which the one or more electrically conductive structure exit the electrically insulating body.

14. A feedthrough for an implantable medical device comprising:
an electrically insulating body including a first surface and a second surface; and
a plurality of electrically conductive structures contiguously extending through and embedded within said electrically insulating body, such that said plurality of electrically conductive structures are circumferentially covered by said electrically insulating body, such that opposing ends of said one or more electrically conductive structures are exposed, and such that said at least one electrically conductive structures extend beyond at least the first or second surface, wherein said electrically conductive structures comprise an electrically conductive metal or metal alloy having a thickness of about 70 microns.

15. The feedthrough of claim 14, wherein said electrically conductive structures have a thickness of between about 40 microns and about 70 microns.

16. The feedthrough of claim 14, wherein said electrically conductive structures have an overall elongate length of at least 7 mm.

17. The feedthrough of claim 14, wherein:
the one or more electrically conductive structures are in direct contact with the electrically insulating body; and
the electrically insulating body is a monolithic body.

18. The feedthrough of claim 15, wherein said electrically conductive structures have a thickness of about 50 microns.

19. A feedthrough for an implantable medical device comprising:
an electrically insulating body including a first surface and a second surface; and
a plurality of electrically conductive structures contiguously extending through and embedded within said electrically insulating body, such that said electrically conductive structures are circumferentially covered by said electrically insulating body such that a hermetic seal is formed between the electrically conductive structures and the electrically insulating body, such that opposing ends of said electrically conductive structures are exposed, and such that said at least one electrically conductive structures extend beyond at least the first or second surface,
wherein said conductive structures comprise an electrically conductive metal or metal alloy.

20. The feedthrough of claim 19, wherein the hermetic seal is located at least an interface between the embedded conductive members and the surrounding insulating member.

21. The feedthrough of claim 19, wherein the hermetic seal is adapted to prevent transfer of fluids from a first side of the feedthrough into which the one or more electrically conductive structures enter the electrically insulating body to a second side of the feedthrough out of which the one or more electrically conductive structure exit the electrically insulating body.

22. The feedthrough of claim 19, wherein the hermetic seal is adapted to prevent transfer of fluids from a first side of the feedthrough into which the one or more electrically conductive structures enter the electrically insulating body, along one or more of the electrically conductive structures, to a second side of the feedthrough out of which the one or more electrically conductive structure exit the electrically insulating body.

23. The feedthrough of claim 19, wherein:
the plurality of electrically conductive structures are in direct contact with the electrically insulating body; and
the electrically insulating body is a monolithic body.

24. An implantable medical apparatus, comprising:
a medical device adapted to be implanted in a human, the medical device including a housing having a housing wall; and
a feedthrough adapted to be implanted in a human, wherein the feedthrough is attached to the housing wall of the medical device, the feedthrough including:
an electrically insulating body; and
a plurality of conductive structures contiguously extending through and embedded within said electrically insulating body, such that said electrically conductive structures are circumferentially covered by said electrically insulating body, and such that opposing ends of said at least one electrically conductive structures are exposed,
wherein the one or more electrically conductive structures comprise an electrically conductive metal or metal alloy,
wherein the feedthrough provides electrical communication from an outside of the housing through the housing wall to an inside of the housing.

25. The feedthrough of claim 22, wherein the hermetic seal is adapted to prevent transfer of fluids from the second side of the feedthrough, along one or more of the electrically conductive structures, to the first side of the feedthrough.

26. The feedthrough of claim 24, wherein:
the plurality of electrically conductive structures are in direct contact with the electrically insulating body; and
the electrically insulating body is a monolithic body.

27. The implantable medical apparatus of claim 24, wherein said electrically conductive structures comprise an electrically conductive metal or metal alloy having a thickness of about 70 microns.

28. The implantable medical apparatus of claim 24, wherein said electrically conductive structures are circumferentially covered by said electrically insulating body such that a hermetic seal is formed between the electrically conductive structures and the electrically insulating body.

29. The implantable medical apparatus of claim 24, wherein the feedthrough is adapted to limit transfer of fluids from a exterior of the housing to an interior of the housing by preventing the transfer of fluids through the feedthrough along one or more of the electrically conductive structures.

30. The implantable medical apparatus of claim 24, wherein the implantable medical apparatus is a cochlear implant hearing prosthesis and the feedthrough provides electrical conduction between the circuitry within an implantable stimulator unit of said prosthesis and one or more intracochlear or extracochlear electrodes and/or an implantable receiver coil.

* * * * *